United States Patent [19]

Taylor

[11] Patent Number: 4,917,776
[45] Date of Patent: Apr. 17, 1990

[54] FLOW THROUGH VOLTAMMETRIC ANALYZER AND METHOD USING DEOXYGENATOR

[76] Inventor: Larry Taylor, P.O. Box 104, Westtown, Pa. 19395

[21] Appl. No.: 308,847

[22] Filed: Feb. 9, 1989

[51] Int. Cl.⁴ .................................. G01N 27/28
[52] U.S. Cl. ........................... 204/153.1; 55/16; 55/36; 55/159; 204/409
[58] Field of Search .............. 55/16, 36, 159; 204/409, 1 T

[56] References Cited

U.S. PATENT DOCUMENTS

| | | | |
|---|---|---|---|
| 3,367,858 | 2/1968 | Kurosaki | 204/413 |
| 3,421,989 | 1/1969 | Haagen-Smit | 204/413 |
| 3,475,310 | 10/1969 | Tyler | 204/402 |
| 3,750,460 | 8/1973 | Vesely et al. | 73/61.1 R |
| 3,808,116 | 4/1974 | Webb | 204/409 |
| 3,857,088 | 12/1974 | Vesely et al. | 324/440 |
| 4,036,704 | 7/1977 | Takata | 204/1 T |
| 4,107,020 | 8/1978 | Brochier et al. | 204/251 |
| 4,138,322 | 2/1979 | Barnes et al. | 204/411 |
| 4,142,944 | 3/1979 | Smith | 204/1 T |
| 4,220,515 | 9/1980 | de Kreuk | 204/409 |
| 4,260,467 | 4/1981 | Smith et al. | 204/413 |
| 4,469,495 | 9/1984 | Hiraizumi et al. | 55/189 |
| 4,490,234 | 12/1984 | Buzza | 204/409 |
| 4,500,411 | 2/1985 | Yarnitzky | 204/413 |
| 4,548,679 | 10/1985 | Guidelli et al. | 204/1 T |
| 4,566,949 | 1/1986 | Berger | 204/1 T |
| 4,601,792 | 7/1986 | Tenygl | 204/1 T |
| 4,661,210 | 4/1987 | Tenygl | 204/1 T |
| 4,662,996 | 5/1987 | Venkatasetty | 204/1 T |
| 4,714,527 | 12/1987 | Hofmeier et al. | 204/1 T |

FOREIGN PATENT DOCUMENTS 248192  7/1987  Fed. Rep. of Germany .

OTHER PUBLICATIONS

Catalog brochure of EG&G Princeton Applied Research for Polarographic Instruments—©1987.
Brochure/Spec. Sheet of Eldex for Metering Pumps Precision Equipment for Chromatography.
Brochure/Spec. Sheet of ISCO, Inc. for ISIS AutoSampler ©1982.

*Primary Examiner*—G. L. Kaplan
*Attorney, Agent, or Firm*—Michael F. Petock

[57] ABSTRACT

A flow through polarographic or other voltammetric analyzer utilizes an improved deoxygenator/pulse dampener in the form of a knitted or other form of convoluted oxygen permeable tubing, such as silicone rubber tubing, through which the flow sample passes. The oxygen permeable tubing is mounted in a chamber containing a flowing inert gas under a positive pressure.

19 Claims, 4 Drawing Sheets

FLOW THROUGH VOLTAMMETRIC ANALYZER AND METHOD USING DEOXYGENATOR

BACKGROUND OF THE INVENTION

The present invention relates to an improved polarographic or other voltammetric flow through apparatus wherein improved results are obtained in the deoxygenation of the sample as well as the dampening of pump pulsations in the sample flow to provide decreased time required per analysis and improved test results.

As utilized herein, voltammetric analysis includes polarographic analysis. As used herein, polarographic analysis is voltammetric analysis utilizing a dropping mercury electrode. Voltammetric analysis is meant to refer herein to electrochemical analysis which utilizes an electrode other than a dropping mercury electrode. The present invention is applicable to both.

Electrochemistry utilizing the dropping mercury electrode polarography and other types of voltammetry is known in the art, for example see *Polarography, Encyclopedia of Chemistry*, 3rd Edition, published by Van Nostrand Reinhold Company, 1973. However, there has been a need in polarography, voltammetry, stripping voltammetry and linear sweep voltammetry to automate sample handling and deoxygenation, particularly when reductive electrochemical determinations are performed. Attempts to automate electrochemical techniques have failed to mechanize the sample handling steps one would do manually. Another problem with manual and the few attempts that automated electrochemical instruments which have been made is the potential exposure of the analyst to solvent vapors and mercury (if a dropping mercury electrode is used).

In some prior art devices, deoxygenation has been performed by bubbling an inert gas through the analyte for four to ten minutes. Vapors from volatile solvents and analytes are released into the laboratory atmosphere creating an exposure for the analyst. The four to ten minutes deoxygenation time lengthens the total analysis time as does manually filling and emptying electrochemical cells.

One attempt at automation is shown by U.S. Pat. No. 4,138,322—Barnes, et al. wherein nitrogen gas is injected into a glass helical coil through which the analyte passes forming bubbles in the flow. These bubbles are then ducted out of the system. In addition to the time factors involved, this may cause the loss of solvent or analyte, particularly where solvent and analyte are volatile. This reduces the accuracy and reproducibility of the electrochemical determination. Furthermore, the analyte may become contaminated during deoxygenation by leakage, since the inert gas is injected directly into the analyte flow stream. Furthermore, such a system does not provide pump pulsation dampening in the glass helical coil.

Other deoxygenation methods have included the use of a gas permeable tube mounted within a vacuum. For example, see German Democratic Republic patent No. DD 248,192 which utilizes a 40 cm. silicone rubber tube and a Smoler capillary and U.S. Pat. No. 4,469,495—Hiraizumi, et al. which utilizes a plurality of spiral turns with spacer elements therebetween in a tank which is under at least a partial vacuum. Other attempts have included the use of a nebulizer, for example see U.S. Pat. No. 4,500,411—Yarnitzky.

The present invention provides a significance improvement over prior art flow though voltammetry analysis apparatus including polarographic analysis apparatus.

SUMMARY OF THE INVENTION

One advantage of the present invention is that it provides a flow through or continuous flow for the analyte and/or electrolyte accomplishing deoxygenation without manual handling of the analyte samples. Another advantage of the present invention is that it provides a means of dampening pump pulsations in the analyte fluid flow thereby providing narrower peaks in the graphic output reading.

Another advantage of the present invention is that it provides a system wherein the permeable tubing of the deoxygenator is under a positive pressure avoiding the possibility of absorption of oxygen from the atmosphere should there be a leak.

Another advantage of the present invention is that the deoxygenator/pulse dampener is utilizable with all types of voltammetry electrochemical analyzers, and it is not limited to one type of device such as a Smoler capillary electrode.

Another advantage of the present invention is that it reduces the time to perform an analysis of a particular analyte.

Another advantage of the present invention is that it produces a highly efficient deoxygenation in a significantly shortened deoxygenation time.

Briefly, in accordance with the present invention, an improved flow through polarographic or voltammetric analysis apparatus is provided with automatic deoxygenation and pump pulsation dampening apparatus. The flow through system comprises a switching valve for selecting analyte or electrolyte, the output of the valve is connected to a pump, which may be a reciprocating, peristaltic or syringe type pump, the output of which is fed through the deoxygenator/pulse dampener. The deoxygenator is comprised of oxygen permeable tubing in which a predetermined length is convoluted, preferably by knitting. The analyte flows through the tubing. The oxygen permeable tubing is mounted in a chamber or the like through which an inert gas, substantially free of oxygen, is passed at a positive pressure. The oxygen from the analyte permeates through the tubing, which is preferably silicone rubber, and is carried away by the inert gas which may be nitrogen, helium or argon. The convoluted or knitted structure of tubing provides a pulse dampening effect wherein the pump pulsations are not noticeable, thereby providing a cleaner output. The output of the deoxygenator/pulse dampener is fed to a flow cell which may contain a dropping mercury electrode or other voltammetric working electrode.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
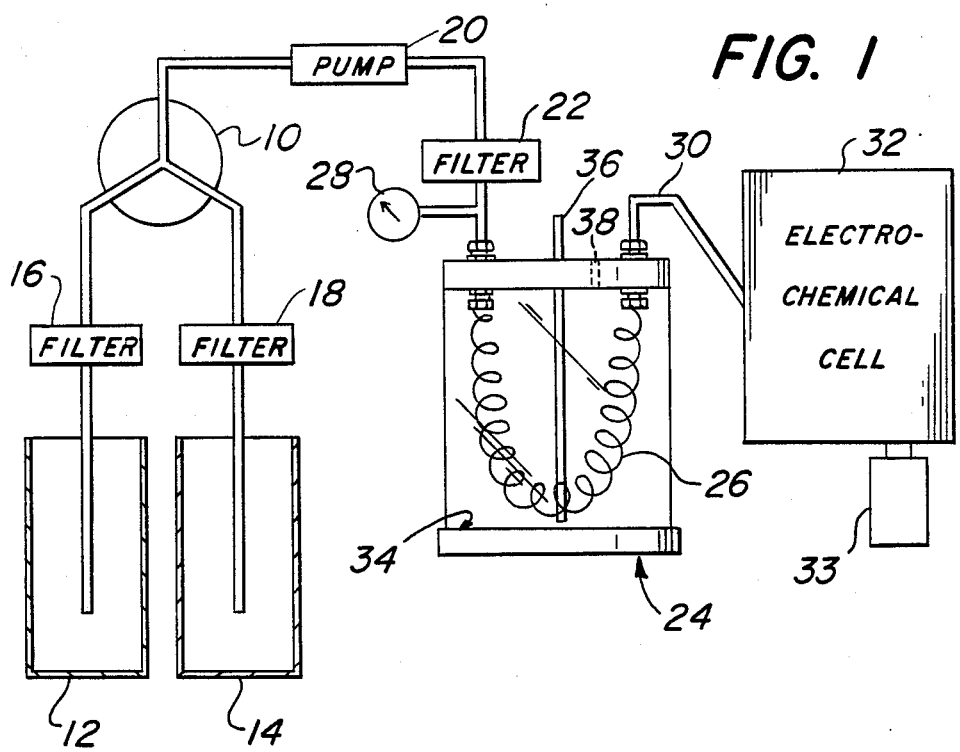
FIG. 1 is a schematic of a flow through voltammetric apparatus in accordance with the present invention.

Referring now to the drawings, wherein like numerals indicate like elements, there is shown in FIG. 1 a flow through voltammetry apparatus with an improved deoxygenator/pulse dampener in accordance with the present invention. There is shown in FIG. 1 a switching or selector valve 10 for selecting analyte reservoir or container 12 or electrolyte reservoir or container 14 through optional filters 16 and 18, respectively. Filters 16 and 18 may be provided to prevent the possibility of solid contaminants, particularly in the analyte, from plugging or causing damage to pump 20. However, in the preferred embodiment, filters 16 and 18 may be eliminated, as they are not necessary in most cases. The analyte contained in reservoir 12 is a solution of the sample to be analzyed plus electrolyte.

Pump 20 may be a low pressure reciprocating, peristaltic or syringe pump which is used to draw analyte or electrolyte from their respective reservoirs 12 and 14 through selector valve 10. Analyte or electrolyte is pumped through filter 22, on the output side of pump 20 and into deoxygenator/pulse dampener 24. Filter 22 removes any particulate matter from the analyte or electrolyte or particulate matter which may be generated as a result of pump seal erosion. Particulate matter, if not removed, may plug the deoxygenator/pulse dampener 24 or downstream tubing which would create high back pressure and could cause rupture of the tubing, including oxygen permeable tubing 26 in deoxygenator/pulse dampener 24. A pressure gauge 28 may be provided to monitor the back pressure in the deoxygenator/pulse dampener.

The flow path of the analyte selected from reservoir 12 or electrolyte selected from reservoir 14 is through the filters 16 or 18, selector or switching valve 10, pump 20, filter 22, oxygen permeable tubing 26 and oxygen impermeable tubing 30 to flow electrochemical cell 32 which may be a dropping mercury electrode cell or any other suitable voltammetric cell.

Figure 3:
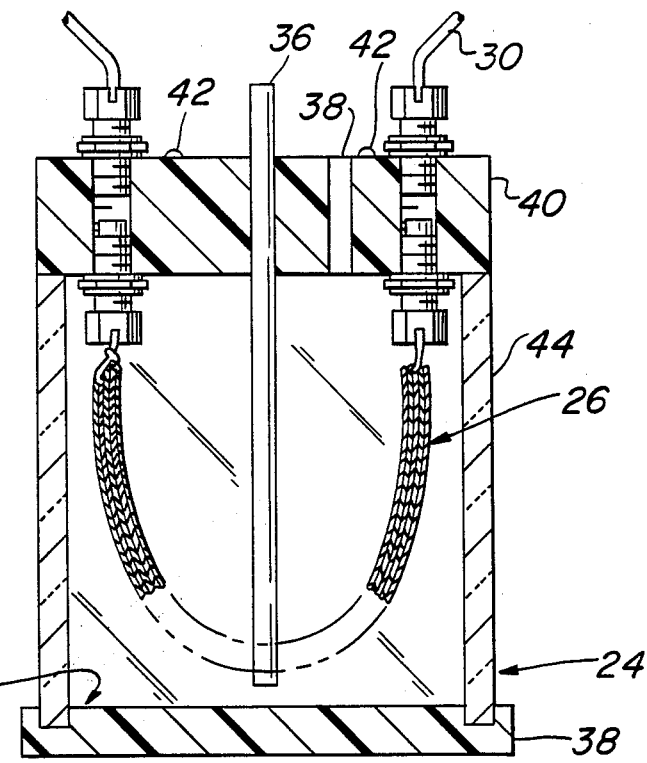
FIG. 3 is a view, partially in cross-section, of a deoxygenator/pulse dampener in accordance with the present invention.
Figure 4:
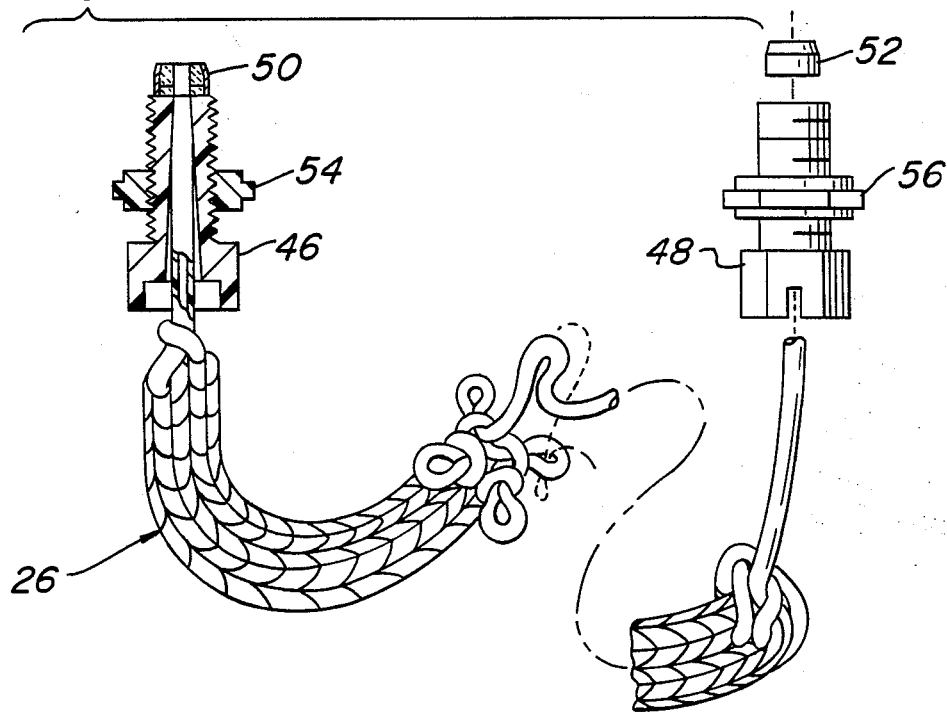
FIG. 4 is an elevation view, partially broken away, showing in greater detail the structure of the convoluted or knitted oxygen permeable tubing of the deoxygenator.

The deoxygenator/pulse dampener 24 and the oxygen permeable tubing 26 are shown in greater detail in FIGS. 3 and 4. Referring now to FIGS. 1, 3 and 4 taken together, the analyte/electrolyte flows through the oxygen permeable tubing 26. The tubing 26 is preferred to be silicone rubber tubing because it provides a greater rate of oxygen diffusion through its walls than other polymeric materials presently available. It is contemplated that other polymeric materials may be utilized in practicing this invention, but the efficiency for oxygen removal is likely to be less than silicone rubber. In selecting a synthetic polymer other than silicone rubber, a polymer should be selected which has a relatively high rate of oxygen diffusion through the material.

As shown in greater detail in FIGS. 3 and 4, the silicone rubber tubing should be convoluted with a large number of convolutions per unit length. In a preferred embodiment, the silicone rubber tubing is knitted to provide a large number of convolutions per unit length and to enable a long length of tubing to be placed within the deoxygenator/pulse dampener 24.

The convoluted or knitted silicone rubber oxygen permeable tubing 26 is mounted in a chamber 34 which is provided with an inert gas via inlet tube 36. The inert gas flows out of outlet 38. The inert gas flowing through chamber 34 is preferably under a slight positive pressure (slightly above atmospheric pressure) which will prevent air (particularly oxygen) from contaminating the chamber if there is a leak, such as by a slightly defective seal. The inert gas may be nitrogen, helium or argon, gases which are commonly available in laboratories today. The gas within chamber 34 must be kept substantially oxygen free for the deoxygenator to operate efficiently. It is preferable that the inert gas contain less than 1 ppm oxygen for the oxygenator to operate with a high efficiency. The inert gas preferably has a rapid flow rate of between 100 to 300 cubic centimeters per minute. This carries away the oxygen after it has been diffused through the oxygen permeable tubing 26 and into the chamber of the deoxygenator 24.

The silicone rubber tubing length, internal diameter and wall thickness affect the rate of diffusion, overall efficiency and pressure stability. The length of the tubing controls the deoxygenation time and efficiency. Longer lengths of tubing increase efficiency, but also increase deoxygenation time. In a preferred embodiment, a 10 foot (300 cm.) length of tubing was used with an inner diameter of 0.015 inch and an outer diameter of 0.0625 inch. The deoxygenation time in this preferred embodiment was 0.5 minute and the deoxygenation efficiency was greater than 99.5%. Although preferred flow rates of inert gas, preferred allowable degree of oxygen impurity of the inert gas, preferred silicone rubber tubing dimensions and other preferred parameters have been given, it is understood that the invention may be practiced outside these parameters within the spirit of the present invention.

In the preferred embodiment, the silicone rubber tubing was knitted as shown in greater detail in FIG. 4. It is understood that other forms of convoluting the tubing to provide a large number of convolutions per unit length also fall within the scope of the present invention. The knitting as described in the preferred invention, prevents the analyte passing through the tubing from diffusing and becoming more dilute. Compared to an equal length of straight tubing, knitted tubing provides 30% greater sensitivity. Another advantage of the knitting is that it allows long lengths of tubing to be packed into a small chamber volume, as compared to straight tubing. A smaller chamber volume reduces the flow of gas needed to keep the chamber oxygen free and reduces the time needed to deoxygenate the chamber. The inert gas flow at a positive pressure provides significant advantages over a partial vacuum approach. First, frequent maintenance of seals is required in a partial vacuum apparatus to prevent the leakage of air into the chamber which would decrease the deoxygenation efficiency. An inert gas purge with a positive pressure prevents air from contaminating the deoxygenator. An oxygen scavenging device may be utilized on the inlet lines of the deoxygenator to prevent air from contaminating the inert gas before it enters the deoxygenation chamber and to eliminate any oxygen impurity that may be in the inert gas. Another advantage of the use of an inert gas under positive pressure, as compared to a vacuum or partial vacuum, is that it decreases the possibility of rupturing the oxygen permeable tubing 26.

Referring still to FIGS. 3 and 4, a preferred embodiment of the deoxygenation chamber is disclosed. The deoxygenation chamber 34 may be comprised of synthetic material, glass or other suitable material. However, in the preferred embodiment shown, a synthetic or plastic material is utilized to form the base 38 and a detachable top 40. The detachable top 40 is fastened to the chamber with four screws 42 (two of which are shown). Sidewall 44 is preferably comprised of a transparent material such as glass which allows viewing of the oxygen permeable tubing 26 within the deoxygenation chamber 34. This structure allows easy access for replacement of oxygen permeable tubing in the deoxygenator/pulse dampener. The deoxygenator tubing 26 is mounted to connectors 46 and 48 as shown, wherein connector 46 is shown in cross-section. The tubing is mounted to the connector by use of ferrules 50 and 52 as is well known in the art. The connectors 46 and 48 are mounted by their threaded surfaces in detachable top 40 and are locked by means of nuts 54 and 56.

The knitted oxygen permeable tubing of silicone rubber in the present invention is effective in substantially eliminating band spreading which has been a common problem in prior art devices. The knitted tubing produces sharper peaks. The knitted tubing is easily replaced by removal of the detachable top 40 in the deoxygenator/pulse dampener of the present invention. The knitted tubing also provides a pulse dampening effect wherein analyte pulsations caused by a peristaltic, syringe or reciprocating pump are not noticeable, and therefore provide enhanced outputs on the polarographic or other voltammetric apparatus.

The selector valve 10 allows the switching between samples, standards and electrolyte depending on the type of valve chosen. Also the use of a valve permits the addition of an autosampler to the system. The pump choice has flexibility by allowing the mixing of two streams. Further, by the use of selectively passing pure electrolyte through the system, the system is automatically flushed or cleaned wherein subsequent samples may be run without contamination from a previous sample, all without the need of manual cleaning.

Figure 5A:
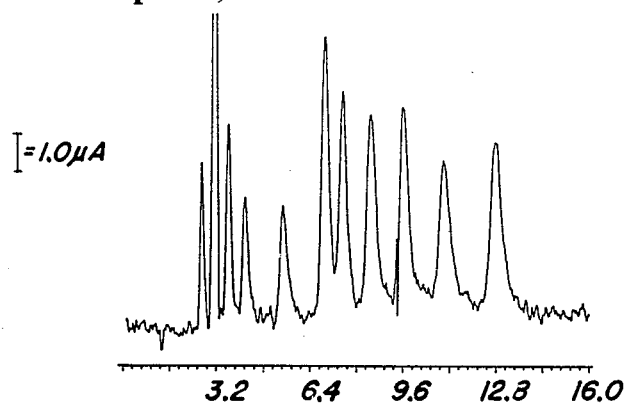
FIGS. 5a and 5b are wave forms of an output of a voltammetric analyzer, FIG. 5a being without the use of the deoxygenator/pulse dampener of the present invention and FIG. 5b showing the results on the same sample with the use of the deoxygenator/pulse dampener of the present invention.
Figure 5B:
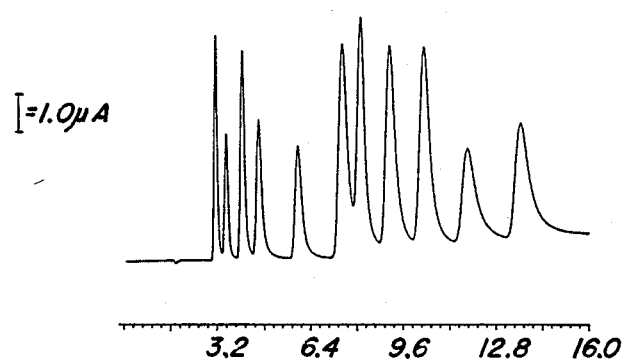

Referring now to FIGS. 5a and 5b, there is shown in FIGS. 5a and 5b output graphs for a voltammetric analyzer utilizing a liquid chromatographic column in the flow path located before the deoxygenator wherein a 10 microliter injection of 11 aromatic nitrocompounds at a concentration of 18 to 70 ppm wherein the electrochemical detector was mercury plated gold at $-0.90$ volts versus Ag/AgCl. The y axis is plotted in microamperes as shown with the x axis showing retention time in minutes. FIG. 5a shows an output graph without the use of the deoxygenator which shows substantial noise and FIG. 5b shows the output with the use of the deoxygenator of the present invention wherein a much cleaner output signal is produced. Without the deoxygenator of the present invention, there were ragged base lines, excessive background current, large peaks that mask other analytes and reduced potential range. As shown in FIG. 5b, the dissolved oxygen which caused the problems has been eliminated.

Figure 6A:
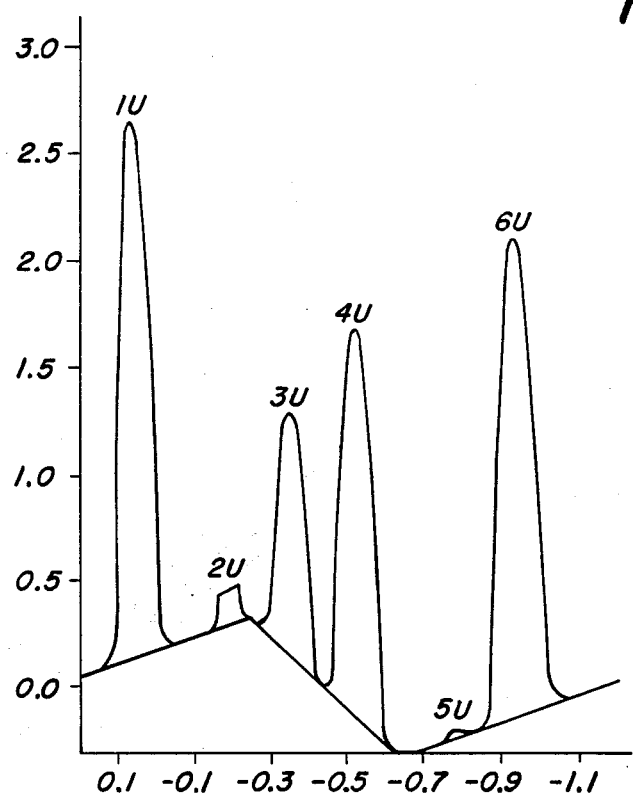
FIGS. 6a and 6b are outputs of a polarograph, FIG. 6a showing the output of a sample utilizing flow polarography in accordance with the present invention and FIG. 6b illustrating an output utilizing quiescent polarography.
Figure 6B:
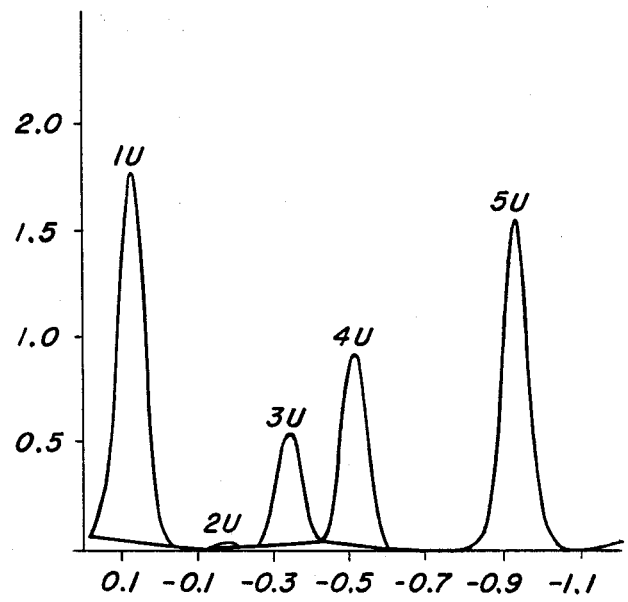

Referring to FIGS. 6a and 6b, 6a is an output graph showing the use of flow polarography in accordance with the present invention whereas FIG. 6b is the output graph of the same sample run on quiescent polarography. In FIG. 6a using the polarography of the present invention, the figure shows that at a flow rate of 1.0 ml/min., the peak heights are increased without any increase in base line noise. FIGS. 6a and 6b show that with nonturbulent and pulseless flow, polarography can be done in a flowing stream. For the flow polarography polarogram in FIG. 6a, the buffer was not purged to remove oxygen before running the polarogram. Thus the time required to run the polarogram shown in FIG. 6a was 6.6 minutes. The conventional polarogram shown in FIG. 6b required 10 minutes because the solution had to be purged of oxygen. This illustrates an advantage of the present invention gained by online deoxygenation and flow polarography in accordance with the present invention.

Figure 7:
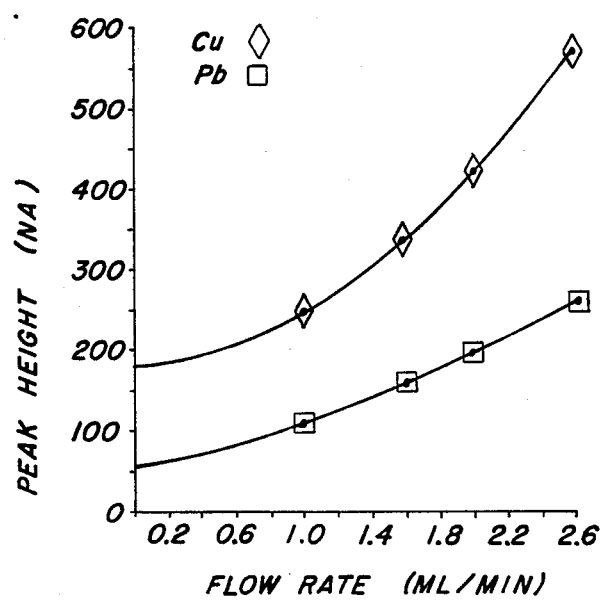
FIG. 7 is a graph of flow rate versus peak height utilizing flow polarography.

FIG. 7 is another chart in which peak height in nanoamperes as plotted on the y axis versus flow rate in milliliters per minute on the x axis. This figure shows the effect of flow rate on peak height for both copper and lead. As may be seen, as the flow rate increases, the peak height increases. In producing the graph in FIG. 7, the test was run using 0.1 m sodium acetate with 0.1 m acetic acid buffer with 1 ppm of copper and lead added.

In another experiment, a polarogram for 37 ppm of lead and cadmium in 0.01 M tartaric acid buffer was run followed by a polarogram for the tartaric acid with no lead and cadmium. No detectable lead or cadmium was found in the blank. At an estimated detection limit of 0.05 ppm, this flow polarography device has the ability to reduce carryover (from one sample to the next) to less than 0.1%.

Figure 2:
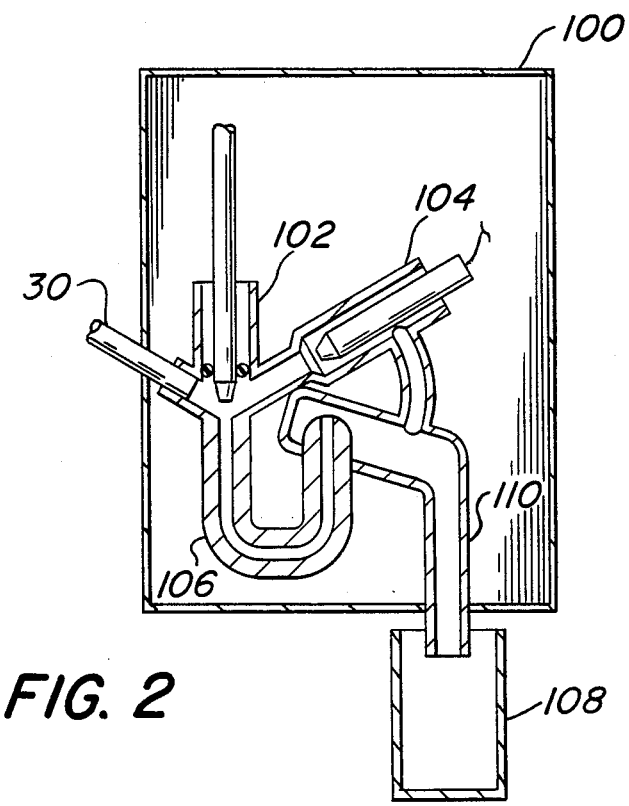
FIG. 2 is a cross-sectional view of one form of flow electrochemical cell which utilizes a dropping mercury electrode.

FIG. 2 shows one possible flow cell or electrochemical cell 100 which may be utilized as the flow cell or electrochemical cell 32 in FIG. 1. As shown in FIG. 1 the flow cell or electrochemical cell has a waste reservoir 33 for sample and mercury waste.

Flow cell 100 receives analyte and/or electrolyte via conduit 30 which is oxygen impermeable. The analyte flowing into electrochemical cell 100 via conduit 30 encounters a dropping mercury electrode 102. A counter and reference electrode 104 is provided as shown and for the conventional purpose of polarography as is well known. A mercury siphon tube 106 is utilized to draw used mercury into waste reservoir 108 via conduit 110. It is understood that other types of flow cells or electrochemical cells may be utilized in practicing the present invention.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A flow through voltammetric analyzer, comprising:
   an electrochemical flow cell;
   a selector valve for selecting an analyte or electrolyte into a flow path;
   a pump for pumping fluid in the flow path;

a deoxygenator in the flow path comprised of a length of convoluted oxygen permeable tubing contained in a container which is sealed except for an inlet and an outlet connection for said tubing and an inlet and an outlet for an inert gas substantially free of oxygen; and means for connecting said outlet connection for said tubing to said electrochemical flow cell.

2. Apparatus in accordance with claim 1 wherein said pump is a peristaltic pump.

3. Apparatus in accordance with claim 1 wherein said pump is a reciprocating pump.

4. Apparatus in accordance with claim 1 wherein said pump is a syringe pump.

5. Apparatus in accordance with claim 1 wherein said tubing contains sufficient convolutions to dampen pump pulsations in the flow path.

6. Apparatus in accordance with claim 1 wherein said tubing of said deoxygenator is knitted and provides a dampening of the pump pulsations.

7. Apparatus in accordance with claim 1 wherein said oxygen permeable tubing is comprised of silicone rubber tubing.

8. Apparatus in accordance with claim 7 wherein said silicone rubber tubing is knitted.

9. Apparatus in accordance with claim 8 including an inert gas source for providing an inert gas wherein said inert gas is selected from the group consisting of nitrogen, helium and argon.

10. Apparatus in accordance with claim 1 wherein said voltammetric flow cell includes a dropping mercury electrode.

11. Apparatus in accordance with claim 1 wherein said oxygen permeable tubing is comprised of silicone rubber having a length of approximately ten feet with an inner diameter of approximately 0.015 inch and an outer diameter of approximately 0.0625 inch.

12. Apparatus in accordance with claim 1 wherein said length and the amount of convolution of said oxygen permeable tubing are selected such that pulsations in the samples caused substantially by said pump are dampened.

13. Apparatus for deoxygenation of samples to be analyzed in a flow through voltammetric analyzer, comprising:

a length of convoluted oxygen permeable tubing through which the sample to be analyzed passes; and a container in which said oxygen permeable tubing is mounted, said container including an inert gas inlet adapted to be connected to a source of inert gas and an outlet for said inert gas, said inert gas flow through said container flushing oxygen out of said container as oxygen diffuses through said tubing.

14. Apparatus in accordance with claim 13 wherein said oxygen permeable tubing is comprised of silicone rubber tubing.

15. Apparatus in accordance with claim 13 wherein said oxygen permeable tubing is comprised of silicone rubber tubing having a length of about ten feet, an inner diameter of approximately 0.015 inch and an outer diameter of approximately 0.0625 inch.

16. Apparatus in accordance with claim 13 including an inert gas source for providing an inert gas wherein said inert gas is selected from the group consisting of nitrogen, helium and argon.

17. Apparatus in accordance with claim 13 wherein said chamber is a sealed chamber having a removable top with an inlet and outlet connection for said convoluted oxygen permeable tubing and an inlet and outlet connection for said inert gas.

18. A method of deoxygenation and pulse dampening in a flow through voltammetric analyzer, comprising the steps of:

flowing sample to be analyzed through a length of convoluted oxygen permeable tubing contained in a substantially sealed container; and flowing an inert gas through said container wherein oxygen diffusing from the sample through said oxygen permeable tubing is flushed from said container.

19. A method in accordance with claim 18 wherein said flowing of an inert gas through said container flows at a rate of between 100 to 300 cubic centimeters per minute.

* * * * *

UNITED STATES PATENT AND TRADEMARK OFFICE
CERTIFICATE OF CORRECTION

PATENT NO. : 4,917,776
DATED : April 17, 1990
INVENTOR(S) : Larry Taylor

It is certified that error appears in the above-identified patent and that said Letters Patent is hereby corrected as shown below:

Column 1, line 67, delete "significance", and insert
  -- significant --.

Column 6, line 30, delete "m", and insert -- $\underline{m}$ --, in each of
  two instances.

Column 6, line 33, delete "0.01 M", and insert -- 0.1 $\underline{M}$ --.

Signed and Sealed this

Eighth Day of October, 1991

*Attest:*

HARRY F. MANBECK, JR.

*Attesting Officer*     *Commissioner of Patents and Trademarks*